United States Patent [19]

Ondetti et al.

[11] Patent Number: 5,166,143
[45] Date of Patent: Nov. 24, 1992

[54] METHOD FOR PREVENTING ONSET OF RESTENOSIS AFTER ANGIOPLASTY EMPLOYING AN ACE INHIBITOR

[75] Inventors: Miguel A. Ondetti, Princeton; A. K. Gunnar Aberg, Lawrenceville; Patricia Ferrer, Pennington, all of N.J.

[73] Assignee: E. R. Squibb & Sons, Inc., Princeton, N.J.

[21] Appl. No.: 714,479

[22] Filed: Jun. 13, 1991

Related U.S. Application Data

[63] Continuation-in-part of Ser. No. 532,000, May 31, 1990, abandoned.

[51] Int. Cl.⁵ ............................................. A61K 31/675
[52] U.S. Cl. ........................................... 514/89; 514/76
[58] Field of Search ............................ 514/75, 76, 89

[56] References Cited

U.S. PATENT DOCUMENTS

| | | | |
|---|---|---|---|
| 4,337,201 | 6/1982 | Petrillo, Jr. | 548/413 |
| 4,374,829 | 2/1983 | Harris et al. | 514/21 |
| 4,452,790 | 6/1984 | Karanewsky et al. | 514/89 |
| 4,820,732 | 4/1989 | Shell et al. | 514/573 |
| 4,975,444 | 12/1990 | Danilewicz et al. | 514/354 |

OTHER PUBLICATIONS

Powell, J. S., et al., "Inhibitors of Angiotensin-Converting Enzyme Prevent Myointimal Proliferation After Vascular Injury", *Science*, vol. 245, pp. 186–188, Jul. 14, 1989.

"AII is MItogenic for Endothelial Cells", *Clin. Res.*, 36, 1988:259A; April, 1988.

"Exposure of Smooth Muscle Cells to AII Results in Expression of the Proto-Oncogene for PDGF", *J. Clin. Invest.*, 83, April 1989:1419.

"Cilazapril (and Captopril) Reduces the Myointimal Proliferation (Restenosis) in Rat Carotids Subjected to Balloon ANgioplasty", *Clin. Res.*, 37, April 1989:286A.

*Primary Examiner*—Frederick E. Waddell
*Assistant Examiner*—T. J. Criares
*Attorney, Agent, or Firm*—Theodore R. Furman, Jr.

[57] ABSTRACT

A method is provided for preventing or reducing the risk of restenosis following angioplasty by administering an ACE inhibitor such as fosinopril or ceranapril, prior to, during and/or after angioplasty.

6 Claims, No Drawings

METHOD FOR PREVENTING ONSET OF RESTENOSIS AFTER ANGIOPLASTY EMPLOYING AN ACE INHIBITOR

This is a continuation-in-part of U. S. Ser. No. 532,000 filed May 31, 1990 now abandoned.

FIELD OF THE INVENTION

The present invention relates to a method for preventing onset of restenosis after angioplasty by administering an ACE inhibitor, and which is preferably a phosphorus-containing ACE inhibitor.

BACKGROUND OF THE INVENTION

Percutaneous transluminal angioplasty (PTA), defined as any percutaneous transluminal: method of decreasing stenosis within a blood vessel, whether caused by the existence of an atheromatous plaque, thrombosis, embolus, and/or mineral deposit, by any of a number of means such as balloon dilatation, thermal ablation, laser atherectomy, mechanical shaving, extraction, or ultrasonic pulverization, hereinafter referred to as angioplasty, is widely used in the treatment of occlusive vascular disease. However, it has been found that restenosis frequently occurs, and in the case of coronary angioplasty, restenosis occurs in about a third of cases within 6 months of the procedure.

European Patent Application 0219782 to Scholkens (Hoechst) discloses the treatment of atherosclerosis, thrombosis and/or peripheral vascular disease in mammals using an angiotensin converting enzyme (ACE) inhibitor or its physiologically tolerable salts. It further discloses that because ACE is predominantly localized in the luminal plasma membrane of the endothelial cell, ACE inhibitors can interfere in platelet-endothelium interaction. In addition, Scholkens discloses that ACE inhibition potentiates the action of bradykinin (a strong stimulator of prostacyclin release from endothelial cells) by inhibiting its degradation and ACE inhibitors, consequently, have an inhibitory effect on platelet aggregation.

Powell, J. S. et al., "Inhibitors of Angiotension-Converting Enzyme Prevent Myointimal Proliferation After Vascular Injury," *Science*, Vol. 245,186–188 Jul. 14, 1989, disclose that angiotyensin-converting enzyme may participate in modulating the proliferative response of the vascular wall after arterial injury, and inhibition of this enzyme may have therapeutic applications to prevent the proliferative lesions that occur after coronary angioplasty and vascular surgery.

Other references which indicate that ACE inhibitors may prevent restenosis following angioplasty include "AII is Mitogenic for Endothelial Cells" (*Clin. Res.*, 36, 1988:259A); "Exposure of Smooth Muscle Cells to AII Results in Expression of the Proto-Oncogene for PDGF" (*J. Clin. Invest.*, 83, 1989:1419); "Cilazapril (and Captopril) Reduces the Myointimal Proliferation (Restenosis) in Rat Carotids Subjected to Balloon Angioplasty" (*Clin. Res.*, 37, 1989:286A).

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al. discloses phosphonate substituted amino or imino acids and salts thereof and covers (S)-1-[6-amino-2-[[hydroxy(4-phenylbutyl)phosphinyl]-oxy]-1-oxohexyl]-L-proline (SQ 29,852, ceranapril). These compounds are ACE inhibitors useful in treating hypertension.

DESCRIPTION OF THE INVENTION

In accordance with the present invention, a method is provided for preventing onset of or reducing risk of restenosis following angioplasty, wherein a therapeutically effective amount of an ACE inhibitor is administered systemically, such as orally or parenterally.

The ACE inhibitor may be administered prior to, during and/or after the angioplasty procedure.

It is believed that the ACE inhibitor reduces the incidence of restenosis by reducing serum cholesterol and by preventing cell proliferation.

The term "restenosis" as employed herein is as defined by Serruys, P. W., et al., "Indicence of restenosis after successful coronary angioplasty: a time related phenomenon. A quantitative angiographic study in 342 consecutive patients at 1, 2, 3, and 4 months," *Circulation* 1988; 7:361–71.

In preferred embodiments where the patient to be treated in accordance with the present invention is normotensive, the angiotensin converting enzyme inhibitor will preferably be administered in amounts below that required to cause hemodynamic effects, that is below that required to cause a reduction in blood pressure.

Examples of angiotensin converting enzyme inhibitors which may be employed herein include any of those disclosed in U.S. Pat. No. 4,374,829 mentioned above, such as N-(1-ethoxycarbonyl-3-phenylpropyl)-L-alanyl-L-proline, that is, enalapril. Additionally, any of the phosphorus-containing compounds may be employed, such as phosphonate substituted amino or imino acids or salts disclosed in U.S. Pat. No. 4,452,790 such as (S)-1-[6-amino-2-[[hydroxy-(4-phenylbutyl)phosphinyl]oxy]-1-oxohexyl]-L-proline (SQ 29,2852 or ceranapril), phosphinylalkanoyl prolines disclosed in U.S. Pat. No. 4,168,267 mentioned above such as fosinopril, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Pat. Nos. 80822 and 60668; Chugai's MC-838 disclosed in CA. 102:72588v and *Jap. J. Pharmacol.*, 40:373 (1986); Ciba-Geigy's CGS 14824 (3-([1-ethoxycarbonyl-3-phenyl-(1S)-propyl]-amino)-2,3, 4,5-tetrahydro-2oxo-1-(3S)-benzazepine-1 acetic acid HCl) disclosed in U.K. Pat. No. 2103614 and CGS 16,617 (3(S)-[[(1S)-5-amino-1-carboxypentyl]amino]-2,3, 4,5-tetrahydro-2oxo-1H-1-benzazepine-1-ethanoic acid) disclosed in U.S. Pat. No. 4,473,575; cetapril (alacepril, Dainippon) disclosed in *Eur. Terap. Res.*, 39:671 (1986); 40:543 (1986); ramipril (Hoechst) disclosed in Eur. Patent No. 79-022 and *Curr. Ther. Res.*, 40:74 (1986); Ru 44570 (Hoechst) disclosed in *Arzneimittelforschung*, 35:1254 (1985), cilazapril (Hoffman-LaRoche) disclosed in *J. Cardiovasc. Pharmacol.*, 9:39 (1987) ; R$_o$ 31-2201 (Hoffman-LaRoche) disclosed in *FEBS Lett.*, 165:201 (1984); lisinopril (Merck) disclosed in *Curr. Therap. Res.*, 37:342 (1985) and Eur. patent appl. No. 12-401, indalapril (delapril) disclosed in U.S. Pat. No. 4,385,051; indolapril (Schering) disclosed in *J. Cardiovasc. Phar-* macol., 5:643, 655 (1983); spirapril (Schering) disclosed in *Acta. Pharmacol. Toxicol.*, 59 (Supp. 5):173 (1986); perindopril (Servier) disclosed in *Eur. J. Clin. Pharmacol.*, 1., 31:519 (1987); quinapril (Warner-Lambert) disclosed in U.S. Pat. No. 4,344,949 and CI 925 (Warner-Lambert) ([3S-[2[R(*)R-(*)]]3R(*)]-2-[2-[[1-(ethoxycarbonyl)-3-phenylpropyl]-amino[-1-oxopropyl]-1,2,3,4-tetrahydro-6,7-dimethoxy-3-isoquinolinecarboxylic acid HCl) disclosed in *Pharmacologist*, 26:243, 266 (1984), WY-44221 (Wyeth) disclosed in *J. Med. Chem.*, 26:394 (1983).

Preferred are those ACE inhibitors which contain a phosphorus atom such as phosphonate substituted amino or imino acids, phosphinyl-alkanoyl prolines, phosphinylalkanoyl substituted prolines or phosphonamidates. Most preferred are the ACE inhibitors, fosinopril and ceranopril.

The above-mentioned U.S. patents are incorporated herein by reference.

In carrying out the method of the present invention, the ACE inhibitor is administered to mammalian species, such as dogs, cats, humans, etc., prior to, during and/or after the angioplasty procedure, and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

Thus, for oral administration, a satisfactory result may be obtained employing the ACE inhibitor in an amount within the range of from about 0.01 mg/kg to about 100 mg/kg and preferably from about 0.1 mg/kg to about 5 mg/kg.

A preferred oral dosage form, such as tablets or capsules, will contain the fosinopril or ceranapril in an amount of from about 0.1 to about 500 mg, preferably from about 2 to about 50 mg, and more preferably from about 5 to about 25 mg.

For parenteral administration, the ACE inhibitor will be employed in an amount within the range of from about 0.005 mg/kg to about 10 mg/kg and preferably from about 0.005 mg/kg to about 1.5 mg/kg.

The compositions described above may be administered in the dosage forms as described above in single or divided doses of one to four times daily. It may be advisable to start a patient on a low dose and work up gradually to a high dose.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of the active substances in a conventional liquid vehicle acceptable for pharmaceutical administration so as to provide the desired dosage in one to four teaspoonfuls.

Such dosage forms can be administered to the patient on a regimen of one to four doses per day.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for 4 weeks to 6 months or longer, beginning at the time of the angioplasty procedure. Sustained release forms of such formulations which may provide such amounts biweekly, weekly, monthly and the like may also be employed. A dosing period of at least one to two weeks are required to achieve minimal benefit.

The following Examples represent preferred embodiments of the present invention.

EXAMPLE 1

A ceranapril formulation suitable for oral administration in preventing restenosis after angioplasty is set out below.

1000 tablets each containing 100 mg of (S)-1-[6-amino-2-[[hydroxy(4-phenylbutyl)phos-phinyl]oxy-1-oxohexyl]-L-proline (ceranapril) were produced from the following ingredients.

| | |
|---|---|
| (S)-1-[6-Amino-2-[[hydroxy(4-phenyl-butyl)phosphinyl]oxy-1-oxohexyl]-L-proline (ceranapril) | 100 g |
| Corn Starch | 50 g |
| Gelatin | 7.5 g |
| Avicel (microcrystalline cellulose) | 25 g |
| Magnesium stearate | 2.5 g |

The ceranapril and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 100 mg of active ingredient which is used for inhibiting loss of cognitive functions.

EXAMPLES 2-7

Using the procedures of Example 1, but substituting tricalcium phosphate for corn starch, the following ceranapril formulations were prepared.

|  | Ex. 2 g/1000 tablets | Ex. 3 g/1000 tablets | Ex. 4 g/1000 tablets | Ex. 5 g/1000 tablets | Ex. 6 g/1000 tablets | Ex. 7 g/1000 tablets |
|---|---|---|---|---|---|---|
| Ceranapril | 2.50 (2.5 mg/ tablet) | 5.0 (5.0 mg/ tablet) | 10.0 (10.0 mg/ tablet) | 20.0 (20.0 mg/ tablet) | 40.0 (40.0 mg/ tablet) | 80.0 (80.0 mg/ tablet) |
| Tribasic Calcium Phosphate, NF | 34.13 | 56.0 | 112.0 | 102.0 | 143.0 | 70.0 |
| Microcrystalline Cellulose, NF* | 35.00 | 34.5 | 69.0 | 69.0 | 103.5 | 41.0 |
| Crospovidone, NF | 2.62 | 3.5 | 7.0 | 7.0 | 10.5 | 7.0 |
| Magnesium Stearate, NF | 0.75 | 1.0 | 2.0 | 2.0 | 3.0 | 2.0 |
| TOTAL | 75 | 100 | 200 | 200 | 300 | 200 |

*Preferred brand/grade-Avicel PH 102.

TABLE 1

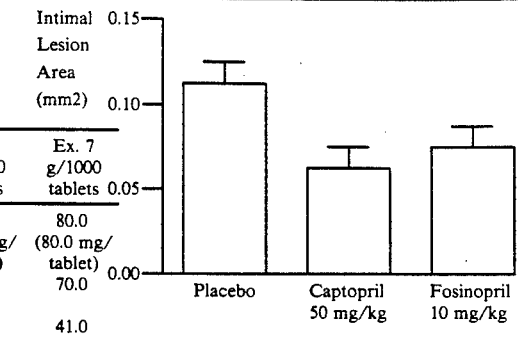

EXAMPLE 8

The effect of captopril and fosinopril on intimal lesion formation in normotensive rats Following procedures of Clowes et al. (*Lab Invest.*, 49:208-215, 1983) the following model of arterial injury in the rat was developed and employed. The endothelial layer of the left carotid artery was removed using a balloon catheter. Smooth muscle cell proliferation occurs along the length of the artery in response to the denudation, resulting in an intimal lesion.

The method of denudation was as follows: the left external carotid artery was cannulated with a balloon catheter and passed down the common carotid resulting in removal of the endothelial lining of the common carotid artery. The catheter was removed and the external carotid was tied off. Two weeks following surgery rats were necropsied and the carotid arteries were pressure fixed. Light microscope cross sections of the left carotid artery were prepared and measurements of the medial and intimal areas were made using a digitizing tablet.

Captopril and fosinopril were dosed orally (50 or 10 mg/kg, BID) for one week prior to surgery and for two weeks post surgery. The formation of an intimal lesion was inhibited 42% in the group receiving captopril (50 mg/kg) and by 37% in the group receiving fosinopril (10 mg/kg) (Table 1)

What is claimed is:

1. A method for preventing or reducing the risk of restenosis following angioplasty, which comprises administering to a mammalian specie in need of such treatment of an effective amount of a phosphorus-containing angiotensin converting enzyme inhibitor selected from the group consisting of phosphonate substituted amino acid, phosphonate substituted imino acid, phosphinylalkanoyl proline, phosphinylalkanoyl substituted proline and phosphonamidate.

2. The method of claim wherein said phosphorus-containing angiotensin converting enzyme inhibitor is selected from the group consisting of fosinopril and ceranapril.

3. The method defined in claim wherein the angiotensin converting enzyme inhibitor is administered prior to angioplasty.

4. The method as defined in claim 1 wherein the angiotensin converting enzyme inhibitor is administered during angioplasty.

5. The method as defined in claim 1 wherein the angiotensin converting enzyme inhibitor is administered after angioplasty.

6. The method as defined in claim 1 wherein said angiotensin converting enzyme inhibitor is administered in single or divided doses of from about 0.1 to about 500 mg/one to four times daily.

* * * * *